United States Patent [19]

Ramachandran et al.

[11] Patent Number: 4,539,135

[45] Date of Patent: Sep. 3, 1985

[54] PERFUME-CONTAINING CARRIER FOR LAUNDRY COMPOSITIONS

[75] Inventors: Pallassana Ramachandran, Robbinsville; Paul S. Grand, Highland Park, both of N.J.

[73] Assignee: Colgate Palmolive Co., New York, N.Y.

[21] Appl. No.: 499,926

[22] Filed: Jun. 1, 1983

[51] Int. Cl.[3] .......................... C11D 17/06; C11D 9/44; A61K 7/46; C11B 9/00

[52] U.S. Cl. .......................... 252/174.11; 252/174.25; 252/522 A

[58] Field of Search ...................... 252/174.11, 174.25, 252/522 A

[56] References Cited

U.S. PATENT DOCUMENTS

| | | | |
|---|---|---|---|
| 4,259,373 | 3/1981 | Demessemaekers et al. | 252/90 |
| 4,322,308 | 3/1982 | Hooper et al. | 252/174.11 |
| 4,326,967 | 4/1982 | Melville | 252/174.11 |
| 4,328,114 | 5/1982 | Johnson et al. | 252/174.11 |
| 4,339,356 | 7/1982 | Whyte | 252/522 A |
| 4,394,127 | 7/1983 | Melville | 252/174.11 |
| 4,499,012 | 2/1985 | Farrell | 252/522 A |

FOREIGN PATENT DOCUMENTS

| | | | |
|---|---|---|---|
| 0069840 | 6/1978 | Japan | 252/522 A |
| 0078965 | 6/1980 | Japan | 252/522 A |
| 2066839 | 7/1981 | United Kingdom | 252/174.11 |

OTHER PUBLICATIONS

"Formation and Properties of Clay-Polymer Complexes", by B. K. G. Theng, Elsevier Scientific Publishing Company, New York, pp. 37–39, 82–87 and 95, (1979).

*Primary Examiner*—John E. Kittle
*Assistant Examiner*—Mukund J. Shah
*Attorney, Agent, or Firm*—Bernard Lieberman; Murray M. Grill; Herbert S. Sylvester

[57] ABSTRACT

A particulate laundry detergent composition is provided comprising:

(a) from about 0.1 to about 50%, by weight, of a perfume-containing carrier comprising (i) discrete particles containing at least 75%, by weight, of a clay mineral other than talc and/or a zeolite, and less than about 5%, by weight, of surface active detergent compounds; and (ii) a perfume, said perfume being adsorbed and/or absorbed on said particles; and (b) from about 2 to about 50%, by weight, additional to any detergent compound in said particles, of one or more surface active detergent compounds selected from the group consisting of anionic, nonionic, cationic, ampholytic and zwitterionic detergent compounds. The balance of the composition is comprised of water and optionally builder and filler salts.

16 Claims, No Drawings

PERFUME-CONTAINING CARRIER FOR LAUNDRY COMPOSITIONS

CROSS REFERENCE TO RELATED APPLICATION

This application is related to copending U.S. application Ser. No. 3,875 (B), filed on even date herewith, which describes a perfume-containing carrier comprising a perfume; discrete particles containing a clay mineral other than talc and/or a zeolite; and a fabric adhesive agent comprising at least one of an anionic detergent compound, a nonionic detergent compound and a defined cationic compound.

BACKGROUND OF THE INVENTION

This invention relates to perfume-containing carriers which significantly enhance the substantivity of perfume to laundered fabrics. More particularly, this invention relates to particulate detergent compositions which include as a component thereof a perfume-containing carrier which is able to impart a pleasing perfume fragrance to the finished laundered fabrics with only minimal amounts of perfume.

Perfume substances which modify or enhance the aroma of detergent compositions or impart a pleasing aroma thereto are well-known in the art. U.S. Pat. Nos. 4,131,555 and 4,228,026, are illustrative of patents which describe substances intended to impart a pleasing aroma or fragrance to liquid and granular detergent compositions. The described methods of preparation consist of mixing the perfume substances, in solid form, with the prepared detergent compositions to form a homogeneous composition. Perfumes which are in liquid form are conventionally added to liquid detergent compositions as a component thereof or sprayed upon the surface of granular detergent compositions. However, detergent compositions which are thus prepared are unable to impart a perfume fragrance to the fabrics being laundered notwithstanding the enhanced aroma of the composition itself. Primarily, this is because the perfume substances in the detergent composition are rapidly dispersed and diluted during laundering in the aqueous wash solution along with the water-soluble components of the detergent composition. Consequently, only a relatively minor amount of the perfume is available to contact and adhere to the fabric being laundered, the major portion of the perfume being drained from the washing machine with the wash solution during the wash cycle. Moreover, to the extent that some perfume is still in contact with the fabric after the washing operation, it tends to be dissipated subsequently during drying, such as, for example, in a gas or electric dryer in which the washed fabrics are tumbled at relatively high temperatures. As a result, fabrics laundered with conventional detergent compositions generally retain only a very faint perfume fragrance which has no particular aesthetic appeal to the user. There is, therefore, a need in the art for an additive to conventional detergent compositions which can effectively provide a perfume fragrance to fabrics being laundered such that the finished laundered fabrics have added appeal to the user.

U.S. Pat. No. 4,259,373 discloses a fabric conditioning article for use in an automatic washer or dryer consisting of a sealed water-in-soluble pouch containing what is described as a softener/antistat composition. In Example II of the patent, there is described a preparation procedure for such antistat composition wherein clay and solid perfume are mixed and the mixture then blended with sprayed particles of certain quaternary ammonium salts. The resulting composition is then filled into a sealed polyester pouch.

SUMMARY OF THE INVENTION

The present invention provides a particulate laundry detergent composition comprising:

(a) from about 0.1 to about 50%, by weight, of a perfume-containing carrier comprising (i) discrete particles containing at least 75%, by weight, of a clay mineral other than talc and/or a zeolite, and less than about 5%, by weight, of surface active detergent compounds; and (ii) a perfume, said perfume being adsorbed and/or absorbed on said particles;

(b) from about 2 to about 50%, by weight, additional to any detergent compound in said particles, of one or more surface active detergent compounds selected from the group consisting of anionic, nonionic, cationic, ampholytic and zwitterionic detergents;

(c) from about 0 to 70%, by weight, of a detergent builder salt, the balance comprising water and optionally a filler salt.

In accordance with another embodiment of the invention, there is provided a perfume-containing carrier for use in admixture with particulate laundry detergent composition comprising (a) discrete particles containing at least 75%, by weight, of (i) a clay mineral other than talc and/or (ii) a zeolite, and less than about 5%, by weight, of surface active detergent compounds; and (b) a perfume, which perfume is in the liquid state at ambient temperature and is adsorbed and/or absorbed on said particles.

In accordance with the process aspect of the invention, the deposition of perfume on laundered fabrics is effected by contacting the stained and/or soiled materials to be laundered with an aqueous solution or dispersion which contains the above-defined perfume-containing carriers.

The term "perfume" as used herein refers to odoriferous materials which are able to provide a pleasing fragrance to fabrics, and encompasses conventional materials commonly used in detergent compositions to counteract a malodor in such compositions and/or provide a pleasing fragrance thereto. The perfumes are preferably in the liquid state at ambient temperature, although solid perfumes are also useful. Included among the perfumes contemplated for use herein are materials such as aldehydes, ketones, esters and the like which are conventionally employed to impart a pleasing fragrance to liquid and granular detergent compositions. Naturally occuring plant and animal oils are also commonly used as components of perfumes. Accordingly, the perfumes useful for the present invention may have relatively simple compositions or may comprise complex mixtures of natural and synthetic chemical components, all of which are intended to provide a pleasant odor or fragrance when applied to fabrics. The perfumes used in detergent compositions are generally selected to meet normal requirements of odor, stability, price and commercial availability. A description of the materials conventionally used in detergent perfumery is set forth by R. T. Steltenkamp, *The Journal of The American Oil*

*Chemists Society,* Vol. 45, No. 6, pp. 429–432, such disclosure being incorporated herein by reference.

The term "particles" as used throughout the specification and claims with regard to the perfume-containing carrier is intended to encompass a wide variety of particulate matter of differing shape, chemical composition, particle size and physical characteristics, the essential common characteristic being that such particles contain at least 75%, by weight, of a clay mineral and/or a zeolite. The particles are desirably free-flowing in nature. The "weight percent" of the clay mineral and the zeolite refers to the weight of such materials including the water and impurities associated with the particular clay or zeolite employed. Accordingly, the carrier particles may be in the form of finely divided powders, as well as relatively larger-sized granules, beads or agglomerated particles, and may be produced by diverse methods of manufacture such as spray-drying, dry-blending or agglomeration of individual components. Particularly preferred carrier particles for use herein are bentonite agglomerates produced by the method described in U.S. Ser. No. 366,587, filed Apr. 8, 1982, the disclosure of which is incorporated herein by reference. The carrier particles may thus optionally include in addition to the clay mineral and/or zeolite, materials which are compatible with conventional laundering compositions, examples of suitable materials including binding or agglomerating agents, e.g., sodium silicate, dispersing agents, detergent builder salts, filler salts as well as common minor ingredients present in conventional laundry detergent compositions such as dyes, optical brighteners, anti-redeposition agents and the like. For purposes of the invention, the particles should contain less than about 5%, by weight, of surface active detergent compounds, preferably less than about 3%, by weight, and most preferably are substantially free of surfactants.

The term "discrete" as used herein with regard to the particles refers to the fact that such particles are employed in the present invention as individually distinct particles, thus excluding, for example, carrier particles which are encompassed within a matrix of other materials, or which are blended with other ingredients such that the particles become a component of a larger aggregate material rather than being in the form of individual and distinct particles.

The present invention is characterized by an effective perfume-containing carrier wherein the carrier particles contain at least 75%, by weight, preferably at least 75%, by weight, and most preferably, at least 90%, by weight of a clay mineral and/or a zeolite. The major portion of the perfume associated with the carrier, preferably at least 95% thereof, is adsorbed and/or absorbed on said particles, the terms "adsorbed" and "absorbed" being used herein to refer to the physical association of the perfume with the carrier particles. Unlike conventional practice wherein the perfumes added to granular detergent compositions are sprayed upon or otherwise contacted with the water-soluble spray-dried granular powders, the perfumes employed in the present invention are contacted with particles of a clay mineral or zeolite which are, for the most part, water-insoluble. It has been found that the perfume thus associated with the carrier particles remains primarily concentrated upon such particles during laundering rather than being dispersed in the aqueous wash solution. This provides a significant advantage during laundering insofar as the perfume-containing carrier particles in the wash solution are likely to contact the laundered fabrics and be dispersed thereupon, particularly in a washing maching where the wash solution is mechanically drained through the fabric during the wash cycle. The perfume is thus maintained proximate to the finished laundered fabric, preventing the dissipation of the perfume fragrance from such fabrics.

DETAILED DESCRIPTION OF THE INVENTION

The perfume-containing carriers of the invention are intended for use in admixture with particulate detergent compositions for laundering operations. Alternatively, the carriers may be advantageously added to the wash solution separate from the detergent composition, such as, for example, during the rinse cycle of a washing machine. The carriers are comprised of two essential ingredients: a clay mineral and/or a zeolite, and a perfume. The weight ratio of clay mineral or zeolite to perfume in the carriers is generally from about 10:1 to about 200:1 and preferably from about 20:1 to about 100:1. The weight of perfume in the carrier will generally vary within the range of from about 0.2 to 10%, and preferably from about 0.5 to 5%, by weight, thereof. The carriers may be conveniently employed during home laundering as additives to a laundry washing bath which contains a conventional laundry detergent composition as a component thereof. Such fully-formulated detergent compositions generally comprise (a) from about 0.1 to about 50%, by weight, preferably from about 5 to about 30%, by weight, of said perfume-containing carrier; and (b) from about 2 to about 50%, by weight, preferably from about 5 to about 40%, by weight, and most preferably from about 5 to about 30%, by weight, of a surface active agent selected from the group of anionic, nonionic, cationic, ampholytic and zwitterionic detergents. The detergent compositions optionally also contain from 0 to about 70%, by weight, of a detergent builder salt, a concentration of from about 5 to about 50% being particularly preferred. The balance of the composition will predominantly comprise water, filler salts, such as, sodium sulfate, and optionally minor components such as binders, optical brighteners, pigments, dyes and the like which are conventional adjunct materials in detergent formulations.

For purposes of economy it is preferred that the major portion, and in most instances, preferably substantially all, of the perfume contained in the detergent composition be provided by the carriers. However, the detergent compositions useful herein may also include perfumes additional to that employed in conjunction with the above-described carriers to provide a pleasant odor to the wash solution or to the composition itself. The use of additional perfumes may also be advantageous in instances which it is used in conjunction with a limited amount of a more expensive perfume. Thus, for example, it may be economically desirable to utilize a minor amount of a relatively expensive perfume with the carrier of the invention and provide relatively larger amounts of a less expensive perfume to the granular detergent composition as a supplementary fragrance, the latter perfume being added by techniques known in the art, such as, by spraying the granular detergent powder.

The clay minerals which are generally useful herein include a wide variety of materials included among which are smectite-type clays; kaolinite, metakaolin; and attapulgite. Of the above-mentioned types of clay minerals, the smectite-type clays are preferred because they advantageously provide desirable softening effects to the laundered fabrics in addition to serving as a carrier for perfume in accordance with the invention. A detailed description of the various types of clay minerals, all of which may be used in the present invention, is set forth by B. K. G. Theng, *The Chemistry of Clay Organic Reactions,* John Wiley & Sons, (1974) pp. 1–15, such disclosure being incorporated herein by reference.

The crystalline types of zeolite which may be employed herein include those described in "Zeolite Molecular Series" by Donald W. Breck, published in 1974 by John Wiley & Sons, typical commercially available zeolites being listed in Table 9.6 at pages 747–749 of the text, such table being incorporated herein by reference. Zeolite structures of type A are especially desirable and are extensively described in the art; see, for example, page 133 of the aforementioned Breck text as well as U.S. Pat. No. 2,882,243. Type 4A zeolite is advantageously employed, the univalent cation of such zeolite being sodium and the pore size of the zeolite being about 4 Angstroms.

The aforementioned smectite-type clays are three-layer clays characterized by the ability of the layered structure to increase its volume several-fold by swelling or expanding when in the presence of water to form a thixotropic gelatinous substance. There are two classes of smectite-type clays: in the first class, aluminum oxide is present in the silicate crystal lattice; in the second class, magnesium oxide is present in the silicate crystal lattice. Atom substitution by iron, magnesium, sodium, potassium, calcium and the like can occur within the crystal lattice of the smectite clays. It is customary to distinguish between clays on the basis of their predominant cation. For example, a sodium clay is one in which the cation is predominantly sodium. With regard to the present carriers, aluminum silicates wherein sodium is the predominant cation are preferred, such as, for example, bentonite clays. Among the bentonite clays, those from Wyoming (generally referred to as western or Wyoming bentonite) are especially preferred.

Preffered swelling bentonites are sold under the trademark Mineral Colloid, as industrial bentonites, by Benton Clay Company, an affiliate of Georgia Kaolin Co. These materials which are the same as those formerly sold under the trademark THIXO-JEL, are selectively mined and beneficiated bentonites, and those considered to be most useful are available as Mineral Colloid No's. 101, etc. corresponding to THIXO-JELs No's. 1, 2, 3 and 4. Such materials have pH's (6% concentration in water) in the range of 8 to 9.4, maximum free moisture contents of about 8% and specific gravities of about 2.6, and for the pulverized grade at least about 85% (and preferably 100%) passes through a 200 mesh U.S. Sieve Series sieve. More preferable, the bentonite is one wherein essentially all the particles (i.e., at least 90% thereof, preferably over 95%) pass through a No. 325 sieve and most preferably all the particles pass through such a sieve. The swelling capacity of the bentonites in water is usually in the range of 3 to 15 ml/gram, and its viscosity, at a 6% concentration in water, is usually from about 8 to 30 centipoises.

In a particular preferred embodiment of the invention, the carrier particles comprise agglomerates of finely divided bentonite, of particle sizes less than No. 200 sieve, agglomerated to particles of sizes essentially in the No's. 10–100 sieve range, of a bulk density in the range of 0.7 to 0.9 g./ml. and a moisture content of 8 to 13%. Such agglomerates include about 1 to 5% of a binder or agglomerating agent to assist in maintaining the integrity of the agglomerates until they are added to water, in which it is intended that they disintegrate and disperse. A detailed description of the method of preparation of such agglomerates is set forth in the aforementioned U.S. Ser. No. 366,587, filed Apr. 8, 1982 which is incorporated herein by reference.

Instead of utilizing the THIXO-JEL or Mineral Colloid bentonites one may employ products, such as that sold by American Colloid Company, Industrial Division, as General Purpose Bentonite Powder, 325 mesh, which has a minimum of 95% thereof finer than 325 mesh or 44 microns in diameter (wet particle size) and a minimum of 96% finer than 200 mesh or 74 microns diameter (dry particle size). Such a hydrous aluminum silicate is comprised principally of montmorillonite (90% minimum), with smaller proportions of feldspar, biotite and selenite. A typical analysis, on an "anhydrous" basis, is 63.0% silica, 21.5% alumina, 3.3% of ferric iron (as $Fe_2O_3$), 0.4% of ferrous iron (as FeO), 2.7% of magnesium (as MgO), 2.6% of sodium and potassium (as $Na_2O$), 0.7% of calcium (as CaO), 5.6% of crystal water (as $H_2O$) and 0.7% of trace elements.

Although the western bentonites are preferred it is also possible to utilize other bentonites, such as those which may be made by treating Italian or similar bentonites containing relatively small proportions of exchangeable monovalent metals (sodium and potassium) with alkaline materials, such as sodium carbonate, to increase the cation exchange capacities of such products. It is considered that the $Na_2O$ content of the bentonite should be at least about 0.5%, preferably at least 1% and more preferably at least 2% so that the clay will be satisfactorily swelling, with good softening and dispersing properties in aqueous suspension. Preferred swelling bentonites of the types described above are sold under the trade names Laviosa and Winkelmann, e.g., Laviosa AGB and Winkelmann G-13.

The perfume-containing carriers of the invention are prepared by methods which result in substantially all of the perfume contacting the above-described carrier particles and being adsorbed and/or absorbed by such particles. A preferred technique is spraying the perfume upon the surface of the carrier particles. This may be effected by spraying the perfume from a pressurized nozzle so as to produce droplets which contact the surface of the particles, the latter being conveniently on a moving belt, such as, a conveyor belt. Alternatively, the process may be conveniently carried out by spraying the perfume over particles which are contained in a rotary drum or tube inclined at a slight angle, such as, from about 5° to 15°, the rotational speed of such drum or tube being suitable from about 5 to 100 rpm. The range of suitable droplet size for effective spraying may vary from about 10 to about 200 microns in diameter, but preferably should be as small as possible relative to the diameter of the particles being sprayed.

As noted above, the laundry detergent compositions of the invention contain a perfume-containing carrier as herein described in combination with one or more surface active agents selected from the group consisting of anionic, nonionic, cationic, ampholytic and zwitterionic detergents.

Among the anionic surface active agents useful in the present invention are those surface active compounds which contain an organic hydrophobic group containing from about 8 to 26 carbon atoms and preferably from about 10 to 18 carbon atoms in their molecular structure and at least one water-solubilizing group selected from the group of sulfonate, sulfate, carboxylate, phosphonate and phosphate so as to form a water-soluble detergent.

Examples of suitable anionic detergents include soaps, such as, the water-soluble salts (e.g., the sodium, potassium, ammonium and alkanolammonium salts) of higher fatty acids or resin salts containing from about 8 to 20 carbon atoms and preferably 10 to 18 carbon atoms. Suitable fatty acids can be obtained from oils and waxes of animal or vegetable origin, for example, tallow, grease, coconut oil and mixtures thereof. Particularly useful are the sodium and potassium salts of the fatty acid mixtures derived from coconut oil and tallow, for example, sodium coconut soap and potassium tallow soap.

The anionic class of detergents also includes the water-soluble sulfated and sulfonated detergents having an aliphatic, preferably an alkyl radical containing from about 8 to 26, and preferably from about 12 to 22 carbon atoms. (The term "alkyl" includes the alkyl portion of the higher acyl radicals). Examples of the sulfonated anionic detergents are the higher alkyl mononuclear aromatic sulfonates such as the higher alkyl benzene sulfonates containing from about 10 to 16 carbon atoms in the higher alkyl group in a straight or branched chain, such as, for example, the sodium, potassium and ammonium salts of higher alkyl benzene sulfonates, higher alkyl toluene sulfonates and higher alkyl phenol sulfonates.

Other suitable anionic detergents are the olefin sulfonates including long chain alkene sulfonates, long chain hydroxyalkane sulfonates or mixtures of alkene sulfonates and hydroxyalkane sulfonates. The olefin sulfonate detergents may be prepared in a conventional manner by the reaction of $SO_3$ with long chain olefins containing from about 8 to 25, and preferably from about 12 to 21 carbon atoms, such olefins having the formula $RCH{=}CHR_1$ wherein R is a higher alkyl group of from about 6 to 23 carbons and $R_1$ is an alkyl group containing from about 1 to 17 carbon atoms, or hydrogen to form a mixture of sultones and alkene sulfonic acids which is then treated to convert the sultones to sulfonates. Other examples of sulfate or sulfonate detergents are paraffin sulfonates containing from about 10 to 20 carbon atoms, and preferably from about 15 to 20 carbon atoms. The primary paraffin sulfonates are made by reacting long chain alpha olefins and bisulfites. Paraffin sulfonates having the sulfonate group distributed along the paraffin chain are shown in U.S. Pat. Nos. 2,503,280; 2,507,088; 3,260,741; 3,372,188 and German Patent No. 735,096.

Other suitable anionic detergents are sulfated ethoxylated higher fatty alcohols of the formula $RO(C_2H_4O)_mSO_3M$, wherein R is a fatty alkyl of from 10 to 18 carbon atoms, m is from 2 to 6 (preferably having a value from about 1/5 to ½ the number of carbon atoms in R) and M is a solubilizing salt-forming cation, such as an alkali metal, ammonium, lower alkylamino or lower alkanolamino, or a higher alkyl benzene sulfonate wherein the higher alkyl is of 10 to 15 carbon atoms. The proportion of ethylene oxide in the polyethoxylated higher alkanol sulfate is preferably 2 to 5 moles of ethylene oxide groups per mole of anionic detergent, with three moles being most preferred, especially when the higher alkanol is of 11 to 15 carbon atoms. To maintain the desired hydrophile-lipophile balance, when the carbon atom content of the alkyl chain is in the lower portion of the 10 to 18 carbon atom range, the ethylene oxide content of the detergent may be reduced to about two moles per mole whereas when the higher alkanol is of 16 to 18 carbon atoms in the higher part of the range, the number of ethylene oxide groups may be increased to 4 or 5 and in some cases to as high as 8 or 9. Similarly, the salt-forming cation may be altered to obtain the best solubility. It may be any suitably solubilizing metal or radical but will most frequently be alkali metal, e.g., sodium, or ammonium. If lower alkylamine or alkanolamine groups are utilized the alkyls and alkanols will usually contain from 1 to 4 carbon atoms and the amines and alkanolamines may be mono-, di- and tri-substituted, as in monoethanolamine, diisopropanolamine and trimethylamine. A preferred polyethoxylated alcohol sulfate detergent is available from Shell Chemical Company and is marketed as Neodol 25-3S.

The most highly preferred water-soluble anionic detergent compounds are the ammonium and substituted ammonium (such as mono, di and tri-ethanolamine), alkali metal (such as, sodium and potassium) and alkaline earth metal (such as, calcium and magnesium) salts of the higher alkyl benzene sulfonates, olefin sulfonates and higher alkyl sulfates. Among the above-listed anionics, the most preferred are the sodium linear alkyl benzene sulfonates (LABS), and especially those wherein the alkyl group is a straight chain alkyl radical of 12 or 13 carbon atoms.

The nonionic synthetic organic detergents are characterized by the presence of an organic hydrophobic group and an organic hydrophilic group and are typically produced by the condensation of an organic aliphatic or alkyl aromatic hydrophobic compound with ethylene oxide (hydrophilic in nature). Practically any hydrophobic compound having a carboxy, hydroxy, amido or amino group with a free hydrogen attached to the nitrogen can be condensed with ethylene oxide or with the polyhydration product thereof, polyethylene glycol, to form a nonionic detergent. The length of the hydrophilic or polyoxyethylene chain can be readily adjusted to achieve the desired balance between the hydrophobic and hydrophilic groups.

The nonionic detergent employed is preferably a poly-lower alkoxylated higher alkanol wherein the alkanol is of 10 to 18 carbon atoms and wherein the number of moles of lower alkylene oxide (of 2 or 3 carbon atoms) is from 3 to 12. Of such materials it is preferred to employ those wherein the higher alkanol is a higher fatty alcohol of 11 to 15 carbon atoms and which contain from 5 to 9 lower alkoxy groups per mole. Preferably, the lower alkoxy is ethoxy but in some instances it may be desirably mixed with propoxy, the latter, if present, usually being a minor (less than 50%) constituent. Exemplary of such compounds are those wherein the alkanol is of 12 to 15 carbon atoms and which contain about 7 ethylene oxide groups per mole, e.g., Neodol® 25-7 and Neodol 23-6.5, which products are made by Shell Chemical Company, Inc. The former is a condensation product of a mixture of higher fatty alcohols averaging about 12 to 15 carbon atoms, with about 7 moles of ethylene oxide and the latter is a corresponding mixture wherein the carbon atom content of the higher fatty alcohol is 12 to 13 and the number of ethylene oxide groups per mole averages about 6.5. The higher alcohols are primary alkanols. Other examples of such detergents include Tergitol® 15-S-7 and Tergitol 15-S-9, both of which are linear secondary alcohol ethoxylates made by Union Carbide Corporation. The former is a mixed ethoxylation product of an 11 to 15 carbon atom linear secondary alkanol with seven moles of ethylene oxide and the latter is a similar product but with nine moles of ethylene oxide being reacted. Also useful in the present compositions are the higher molecular weight nonionics, such as Neodol 45-11, which are similar ethylene oxide condensation products of higher fatty alcohols, the higher fatty alcohol being of 14 to 15 carbon atoms and the number of ethylene oxide groups per mole being about 11. Such products are also made by Shell Chemical Company.

Zwitterionic detergents such as the betaines and sulfobetaines having the following formula are also useful:

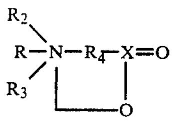

wherein R is an alkyl group containing from about 8 to 18 carbon atoms, $R_2$ and $R_3$ are each an alkyl or hydroxyalkyl group containing about 1 to 4 carbon atoms, $R_4$ is an alkylene or hydroxyalkylene group containing 1 to 4 carbon atoms, and X is C or S:O. The alkyl group can contain one or more intermediate linkages such as amido, ether, or polyether linkages or nonfunctional substituents such as hydroxyl or halogen which do not substantially affect the hydrophobic character of the group. When X is C, the detergent is called a betaine; and when X is S:O, the detergent is called a sulfobetaine or sultaine.

Cationic surface active agents may also be employed. They comprise surface active detergent compounds which contain an organic hydrophobic group which forms part of a cation when the compound is dissolved in water, and an anionic group. Typical cationic surface active agents are amine and quaternary ammonium compounds.

Examples of suitable synthetic cationic detergents include: normal primary amines of the formula $RNH_2$ wherein R is an alkyl group containing from about 12 to 15 atoms; diamines having the formula $RNHC_2H_4NH_2$ wherein R is an alkyl group containing from about 12 to 22 carbon atoms, such as N-2-aminoethyl-stearyl amine and N-2-aminoethyl myristyl amine; amide-linked amines such as those having the formula $R_1CONHC_2H_4NH_2$ wherein $R_1$ is an alkyl group containing about 8 to 20 carbon atoms, such as N-2-amino ethylstearyl amide and N-amino ethylmyristyl amide; quaternary ammonium compounds wherein typically one of the groups linked to the nitrogen atom is an alkyl group containing about 8 to 22 carbon atoms and three of the groups linked to the nitrogen atom are alkyl groups which contain 1 to 3 carbon atoms, including alkyl groups bearing inert substituents, such as phenyl groups, and there is present an anion such as halogen, acetate, methosulfate, etc. The alkyl group may contain intermediate linkages such as amide which do not substantially affect the hydrophobic character of the group, for example, stearyl amido propyl quaternary ammonium chloride. Typical quaternary ammonium detergents are ethyl-dimethyl-stearyl-ammonium chloride, benzyl-dimethyl-stearyl ammonium chloride, trimethyl-stearyl ammonium chloride, trimethyl-cetyl ammonium bromide, dimethyl-ethyl-lauryl ammonium chloride, dimethyl-propyl-myristyl ammonium chloride, and the corresponding methosulfates and acetates.

Ampholytic detergents are also suitable for the invention. Ampholytic detergents are well known in the art and many operable detergents of this class are disclosed by Schwartz, Perry and Berch in the aforementioned "Surface Active Agents and Detergents." Examples of suitable amphoteric detergents include: alkyl betaiminodipropionates, $RN(C_2H_4COOM)_2$; alkyl beta-amino propionates, $RN(H)C_2H_4COOM$; and long chain imidazole derivatives having the general formula:

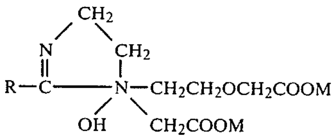

wherein in each of the above formulae R is an acyclic hydrophobic group containing from about 8 to 18 carbon atoms and M is a cation to neutralize the charge of the anion. Specific operable amphoteric detergents include the disodium salt of undecylcycloimidinium-ethoxyethionic acid-2-ethionic acid, dodecyl beta alanine, and the inner salt of 2-trimethylamino lauric acid.

The bleaching detergent compositions of the invention optionally contain a detergent builder of the type commonly used in detergent formulations. Useful builders include any of the conventional inorganic water-soluble builder salts, such as, for example, water-soluble salts of phosphates, pyrophosphates, orthophosphates, polyphosphates, silicates, carbonates, and the like. Organic builders include water-soluble phosphonates, polyphosphonates, polyhydroxysulfonates, polyacetates, carboxylates, polycarboxylates, succinates and the like.

Specific examples of inorganic phosphate builders include sodium and potassium tripolyphosphates, pyrophosphates and hexametaphosphates. The organic polyphosphonates specifically include, for example, the sodium and potassium salts of ethane 1-hydroxy-1,1-diphosphonic acid and the sodium and potassium salts of ethane-1,1,2-triphosphonic acid. Examples of these and other phosphorous builder compounds are disclosed in U.S. Pat. Nos. 3,213,030; 3,422,021; 3,422,137 and 3,400,176. Pentasodium tripolyphosphate and tetrasodium pyrophosphate are especially preferred water-soluble inorganic builders.

Specific examples of non-phosphorous inorganic builders include water-soluble inorganic carbonate, bicarbonate and silicate salts. The alkali metal, for example, sodium and potassium, carbonates, bicarbonates and silicates are particularly useful herein.

Water-soluble organic builders are also useful. For example, the alkali metal, ammonium and substituted ammonium acetates, carboxylates, polycarboxylates and polyhydroxysulfonates are useful builders for the compositions and processes of the invention. Specific examples of acetate and polycarboxylate builders include sodium, potassium, lithium, ammonium and substituted ammonium salts of ethylene diaminetetracetic acid, nitrilotriacetic acid, benzene polycarboxylic (i.e. penta- and tetra-)acids, carboxymethoxysuccinic acid and citric acid.

Water-insoluble builders may also be used, particularly, the complex silicates and more particularly, the complex sodium alumino silicates such as, zeolites, e.g., zeolite 4A, a type of zeolite molecule wherein the univalent cation is sodium and the pore size is about 4 Angstroms. The preparation of such type zeolite is described in U.S. Pat. No. 3,114,603. The zeolites may be amorphous or crystalline and have water of hydration as known in the art.

The use of an inert, water-soluble filler salt is desirable in the laundering compositions of the invention. A preferred filler salt is an alkali metal sulfate, such as, potassium or sodium sulfate, the latter being especially preferred.

Various adjuvants may be included in the laundry detergent compositions of the invention. In general, these include perfumes; colorants, e.g., pigments and dyes; bleaches, such as, sodium perborate, antiredeposition agents, such as, alkali metal salts of carboxymethylcellulose; optical brighteners, such as, anionic, cationic or nonionic brighteners; foam stabilizers, such as alkanolamides, and the like, all of which are well-known in the fabric washing art for use in detergent compositions. Flow promoting agents, commonly referred to as flow aids, may also be employed to maintain the particulate compositions as free-flowing beads or powder. Starch derivatives and special clays are commercially available as additives which enhance the flowability of otherwise tacky or pasty particulate compositions, two of such clay additives being presently marketed under the tradenames "Satintone" and "Microsil".

EXAMPLE 1

Agglomerates of Thixojel No. 1(1) clay were used in the present example and were prepared by the procedure described below wherein the following components were used: Thixojel No. 1 clay (325 mesh) and an aqueous agglomerating solution containing 7% of sodium silicate in a ratio of $Na_2O:SiO_2$ of about 1:2.4.

[1]A tradename of a Wyoming bentonite clay sold by Georgia Kaolin Co., Elizabeth, N.J.

The agglomerates were prepared in a rotary drum characterized by a 19.5 inch diameter, a 23.5 inch length and an axis of rotation adjustable between ten and ninety degrees from the vertical.

9.1 kg. of the Thixojel No. 1 clay was charged into the above-described rotary drum which was aligned at an angle of 20 degrees from the vertical. 3.2 kg. of the aqueous silicate solution at a temperature of 43° C. was sprayed on to the clay while the drum was rotating at about 6 rpm. The axis of the rotary drum was then adjusted to an angle of 70 degrees from the vertical and an additional 3.2 kg. of silicate solution was sprayed on to the clay. The resulting wet agglomerates of clay were transferred in 2 kg. portions to an Aeromatic ST-5 (tradename) fluid bed dryer, manufactured by Aeromatic Corp., Summerville, N.J., and dried to approximately 10 wt.% moisture using an air flow rate of about 6,000 liters per minute and an air inlet temperature of 71° C. Drying was effected in about 15 minutes. The dried material was then passed through a Stokes granulater having a 40 mesh screen, the product particle size being between 40-100 mesh. The fines passing through a 100 mesh screen were recycled to the rotary drum.

A spray dried granular unperfumed detergent composition was used as a component of formulations A, B and C described below and had the following composition:

| Component | Weight Percent |
|---|---|
| Sodium tridecyl benzene sulfonate | 15 |
| Sodium tripolyphosphate | 33 |
| Sodium silicate ($1Na_2O:2.4SiO_2$) | 7 |
| Sodium carbonate | 5 |
| Borax | 2 |
| Sodium sulfate | 27.8 |
| Carboxymethyl cellulose | 0.2 |
| moisture | 10 |

Formulation A—100 grams of the above-described unperfumed detergent composition was blended with 0.2 g. of a conventional detergent-type perfume based on limonene, geraniol, citral, cedrol, benzyl acetate, p-t-butyl cyclohexyl acetate and other aromatic ingredients in a Twin-Shell blender for ten minutes at a blender speed of about 20 rpm.

Formulation B—80 g. of the unperfumed detergent composition described above was blended with 0.2 g. of the same perfume employed in formulation A in accordance with the procedure described above. 19.8 g. of agglomerated Thixojel No. 1 was then added to the blender and mixed with the contents thereof for about 10 minutes at a blender speed of about 20 rpm.

Formulation C—19.8 g. of agglomerated Thixojel No. 1 was blended for about 10 minutes with 0.2 g. of the same perfume used in formulations A and B in the Twin-Shell blender referred to above. Thereafter 80 g. of the unperfumed detergent composition described above was added to the contents of the blender and mixed therewith for about 10 minutes.

Accordingly, formulation A represents a typical conventional detergent formulation containing perfume; formulation B represents a detergent formulation similar to A but which in addition contains clay agglomerates; and formulation C represents a detergent formulation containing the perfume-containing carrier of the invention.

Perfume tests were carried out using cotton, Dacron polyester, and Dacron polyester/cotton (65/35) swatches and terry towels which were washed in a conventional U.S. washing machine at 25° C. using water having a hardness of 100 ppm as calcium carbonate. Each of three sets of the above-described swatches were separately washed using 100 g. of formulations A, B and C, a different formulation being used for each washing.

When the washing procedure was completed, the swatches were evaluated and the fabrics washed in formulation C were found to retain the most perfume fragrance relative to the fabrics washed in formulations A and B.

Based on the above, the use of the perfume-containing carrier for the invention in a granular detergent composition results in a significant increase in the retention of a perfume fragrance on the laundered fabrics.

What is claimed is:

1. A particulate laundry detergent composition comprising:

(a) from about 0.1 to about 50%, by weight, of a perfume-containing carrier consisting essentially of (i) discrete particles containing at least about 90%, by weight, of a smectite-type clay and/or a zeolite, and less than about 5%, by weight, of surface active detergent compounds; and (ii) a perfume;

(b) from about 2 to about 50%, by weight, additional to any detergent compound in said particles, of one or more surface active detergent compounds selected from the group consisting of anionic, nonionic, cationic, ampholytic and zwitterionic detergents;

(c) from about 0 to about 70%, by weight, of a detergent builder salt;

(d) the balance comprising water and optionally a filler salt.

2. A particulate laundry detergent composition in accordance with claim 1 wherein said perfume is adsorbed and/or absorbed on said particles.

3. A particulate laundry detergent composition in accordance with claim 1 which additionally contains a second perfume to supplement the fragrance provided by said perfume-containing carrier.

4. A laundry detergent composition in accordance with claim 1 wherein said builder salt is present in an amount of from about 5 to about 50%, by weight.

5. A laundry detergent composition in accordance with claim 1 wherein said smectite-type clay is a bentonite clay.

6. A laundry detergent composition in accordance with claim 1 wherein the weight ratio of the clay and/or zeolite to perfume in said carrier is from about 10:1 to about 200:1.

7. A laundry detergent composition in accordance with claim 1 wherein the weight of perfume in the carrier is from about 0.2 to about 10%, by weight.

8. A laundry detergent composition in accordance with claim 1 wherein said particles contain a zeolite.

9. A process for depositing perfume on fabrics during laundering which comprises contacting the stained and/or soiled fabrics to be laundered with an aqueous solution or dispersion which contains a perfume-containing carrier consisting essentially of (i) discrete particles containing at least 90%, by weight, of a smectite-type clay and/or a zeolite and less than about 5%, by weight, of surface active detergent compounds; and (ii) a perfume; said perfume being adsorbed and/or absorbed on said particles.

10. A process in accordance with claim 9 wherein said aqueous solution or dispersion contains a particulate laundry detergent composition comprising:

(a) from about 0.1 to about 50%, by weight, of said perfume-containing carrier;

(b) from about 2 to about 50%, by weight, additional to any detergent compound in said carrier, of one or more surface active detergent compounds selected from the group consisting of anionic, cationic, nonionic, ampholytic and zwitterionic detergents; and (c) from about 0 to about 70%, by weight, of a detergent builder salt.

11. A process in accordance with claim 9 wherein said smectite-type clay is a bentonite clay.

12. A process in accordance with claim 9 wherein said particles contain a zeolite.

13. A perfume-containing carrier for use in admixture with a particulate detergent composition or an an additive to a wash solution separate from the detergent composition, said carrier consisting essentially of: (i) discrete particles containing at least 90%, by weight, of a smectite-type clay and/or a zeolite, and less than about 5%, by weight, of surface active detergent compounds; and (ii) a perfume, which perfume is in the liquid state at ambient temperature and is adsorbed and/or absorbed on said particles.

14. A perfume-containing carrier as in claim 13 wherein said smectite-type clay is a bentonite clay.

15. A perfume-containing carrier as in claim 13 wherein the weight ratio of said clay and/or zeolite to perfume in said carrier is from about 10:1 to about 200:1.

16. A perfume-containing carrier as in claim 13 wherein the weight of perfume in the carrier is from about 0.2 to about 10%, by weight.

* * * * *